(12) United States Patent
Hara et al.

(10) Patent No.: US 8,586,741 B2
(45) Date of Patent: Nov. 19, 2013

(54) METHOD FOR PRODUCING DICHLOROPYRAZINE DERIVATIVE

(75) Inventors: Tamio Hara, Takaoka (JP); Naoki Norimatsu, Takaoka (JP); Hiroaki Kurushima, Takaoka (JP); Takuya Kano, Takaoka (JP)

(73) Assignee: Nippon Soda Co., Ltd., Tokyo (JP)

( * ) Notice: Subject to any disclaimer, the term of this patent is extended or adjusted under 35 U.S.C. 154(b) by 0 days.

(21) Appl. No.: 13/144,735

(22) PCT Filed: Jan. 14, 2010

(86) PCT No.: PCT/JP2010/000177
§ 371 (c)(1),
(2), (4) Date: Jul. 15, 2011

(87) PCT Pub. No.: WO2010/087117
PCT Pub. Date: Aug. 5, 2010

(65) Prior Publication Data
US 2011/0275817 A1    Nov. 10, 2011

(30) Foreign Application Priority Data
Jan. 28, 2009   (JP) .................................. 2009-016221

(51) Int. Cl.
*C07D 241/16*   (2006.01)

(52) U.S. Cl.
USPC ....................................................... 544/409

(58) Field of Classification Search
USPC ....................................................... 544/409
See application file for complete search history.

(56) References Cited

FOREIGN PATENT DOCUMENTS

| | | |
|---|---|---|
| EP | 1 256 588 | 11/2002 |
| WO | 01/60834 | 8/2001 |

OTHER PUBLICATIONS

Sato, Nobuhiro, "Studies on Pyrazines. 13[1]. Chlorination of 1-Hydroxy-2(1H)-pyrazinones with Phosphoryl Chloride. Formation of 2,5-Dichloro-3-phenylpyrazine from 1-Hydroxy-3-phenyl-2(1H)-pyrazinone", Journal of Heterocyclic Chemistry, 1986, vol. 23, No. 1, pp. 149-151.

Ohta, Akihiro, et al., "Conversion of 2,5-Diphenyl- and 2,5-Dibenzyl-pyrazines to 2,5-Diketopi-perazines", Chemical & Pharmaceutical Bulletin, 1979, vol. 27, No. 12, pp. 2980-2987.

Ohta, Akihiro, et al., "Syntheses and Reactions of Some 2,5-Disubstituted Pyrazine Monoxides", Chemical & Pharmaceutical Bulletin, 1979, vol. 27, No. 9, pp. 2027-2041.

International Search Report issued for PCT/JP2010/000177, mailed on Mar. 30, 2010, 7 pages.

EP Communication including Supplementary European Search Report from EP Appln. No. 10735589.3, May 28, 2013, 4 pages.

Jones, James Holden et al., "Pyrazine Diuretics. VII. N-Amidino-3-substituted Pyrazinecarboxamides", Journal of medicinal Chemistry, 12(2), 285-7 CODEN: JMCMAR; ISSN: 0022-2623, Mar. 1969, XP002696280, 3 pages.

*Primary Examiner* — Brian McDowell
(74) *Attorney, Agent, or Firm* — Kenyon & Kenyon LLP

(57) ABSTRACT

A method for producing a hydroxypyrazine derivative represented by formula (I) (wherein $R^1$ represents a halogen atom), the method including reacting a pyrazine derivative represented by formula (III) (wherein $R^2$ represents a nitrile group, an N-unsubstituted or N-substituted carbamoyl group, an ester group or a carboxyl group, M represents a cation capable of forming a salt, and n represents a number corresponding with the valence of M) with a halogenating agent. Also, a method for producing a dichloropyrazine derivative represented by formula (II) (wherein $R^{21}$ represents a nitrile group, an N-unsubstituted or N-substituted carbamoyl group, an ester group, a carboxyl group, or a group formed as a result of a change in the functional group of $R^2$ during chlorination), the method including reacting the hydroxypyrazine derivative (I) with a chlorinating agent.

2 Claims, No Drawings

METHOD FOR PRODUCING DICHLOROPYRAZINE DERIVATIVE

TECHNICAL FIELD

The present invention relates to a method for producing a dichloropyrazine derivative that is useful as an intermediate for an agrochemical or pharmaceutical product, and a method for producing a hydroxypyrazine derivative that functions as a production intermediate for the dichloropyrazine derivative.

Priority is claimed on Japanese Patent Application No. 2009-016221, filed Jan. 28, 2009, the content of which is incorporated herein by reference.

BACKGROUND ART

Compounds represented by formula (IV) below are known to be very effective against a variety of viruses, and particularly the influenza virus.

[Chemical Formula 1]

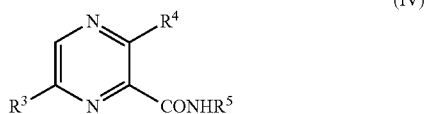

(IV)

(wherein $R^3$ represents a hydrogen atom or a halogen atom, $R^4$ represents a hydroxyl group that may be protected, and $R^5$ represents a hydrogen atom, an acyl group or a carbamoylalkyl group.)

Of these compounds, the 6-fluoro-substituted pyrazinecarboxamide derivative represented by formula (V) (wherein the formula in parentheses represents the tautomer) exhibits powerful anti-influenza activity, and is an excellent antiviral agent (see Patent Document 1).

[Chemical Formula 2]

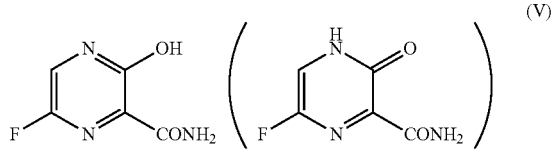

(V)

A number of methods for producing this compound are disclosed in Patent Document 1. Of these, the production method represented by the reaction sequence shown below exhibits a comparatively superior yield.

[Chemical Formula 3]

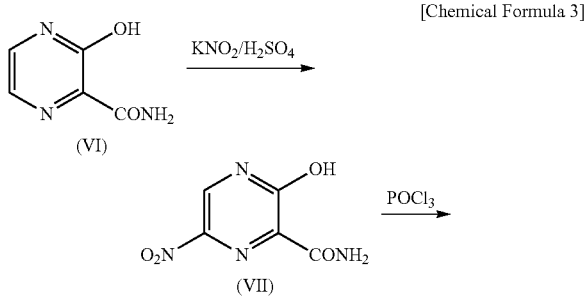

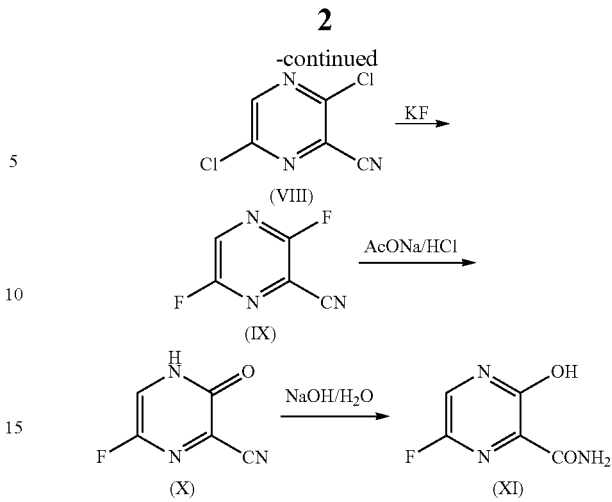

CITATION LIST

Patent Documents

[Patent Document 1] WO01/60834

DISCLOSURE OF INVENTION

Problems to be Solved by the Invention

However, the reaction sequence shown above includes a nitration reaction (the reaction to produce the compound represented by formula (VII) from the compound represented by formula (VI)) that suffers from a danger of explosion, and therefore performing the above production on an industrial scale requires explosion-proof equipment and the like, which is disadvantageous in terms of achieving production at low cost.

An object of the present invention is to provide a method for producing a dichloropyrazine derivative typified by the compound represented by formula (VIII) which does not include a nitration reaction and enables the dichloropyrazine derivative to be produced efficiently and at low cost.

Another object of the present invention is to provide a method for producing a hydroxypyrazine derivative that functions as a production intermediate for the above dichloropyrazine derivative which enables the hydroxypyrazine derivative to be produced efficiently and at low cost.

Means to Solve the Problems

As a result of intensive investigation aimed at achieving the above objects, the inventors of the present invention discovered that brominating a salt of the compound (VI) readily yielded a brominated product, and that by reacting this brominated product with a chlorinating agent, the compound represented by formula (VIII) could be produced at high yield, and they were thus able to complete the present invention.

In other words, the present invention provides the aspects described below.

<1> A method for producing a dichloropyrazine derivative represented by formula (II), the method including reacting a hydroxypyrazine derivative represented by formula (I) with a chlorinating agent.

[Chemical Formula 4]

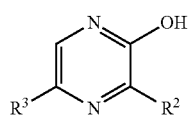

(I)

(wherein $R^1$ represents a halogen atom, and $R^2$ represents a nitrile group, an N-unsubstituted or N-substituted carbamoyl group, an ester group or a carboxyl group.)

[Chemical Formula 5]

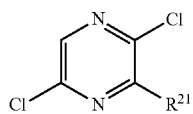

(II)

(wherein $R^{21}$ represents a nitrile group, an N-unsubstituted or N-substituted carbamoyl group, an ester group, a carboxyl group, or a group formed as a result of a change in the functional group of $R^2$ during chlorination.)
<2> A method for producing a hydroxypyrazine derivative represented by formula (I), the method including reacting a pyrazine derivative represented by formula (III) with a halogenating agent.

[Chemical Formula 6]

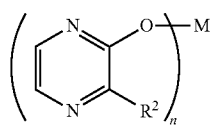

(III)

(wherein $R^2$ represents a nitrile group, an N-unsubstituted or N-substituted carbamoyl group, an ester group or a carboxyl group, M represents a cation capable of forming a salt, and n represents a number corresponding with the valence of M.)
<3> The method for producing a hydroxypyrazine derivative according to <2>, wherein M is a cation formed from a metal element belonging to group I, group IIa or group IIIa of the periodic table of elements.
<4> The method for producing a dichloropyrazine derivative according to <1>, wherein the hydroxypyrazine derivative represented by formula (I) is a compound obtained by reacting a pyrazine derivative represented by formula (III) with a halogenating agent.

Effects of the Invention

The production method of the present invention does not include a nitration reaction that suffers from a danger of explosion, and therefore can be performed without requiring explosion-proof equipment or the like, even in the case of industrial production. According to the production method of the present invention, a dichloropyrazine derivative that is useful as an intermediate for agrochemicals or pharmaceutical products such as antiviral agents, and a hydroxypyrazine derivative that functions as a production intermediate for the dichloropyrazine derivative can be obtained at low cost, with comparative ease, and in high yield.

EMBODIMENTS FOR CARRYING OUT THE INVENTION

Detailed descriptions of the method for producing a dichloropyrazine derivative according to the present invention, and the method for producing a hydroxypyrazine derivative that functions as a production intermediate for the dichloropyrazine derivative are presented below.
<Method for Producing Dichloropyrazine Derivative>
The method for producing a dichloropyrazine derivative according to the present invention includes reacting a hydroxypyrazine derivative represented by formula (I) with a chlorinating agent.
In formula (I), $R^1$ represents a halogen atom. Examples of the halogen atom include a fluorine atom, a chlorine atom, a bromine atom and an iodine atom. Of these, a bromine atom or a chlorine atom or the like is preferred.
In formula (I), $R^2$ represents a nitrile group (a group represented by —CN), an N-unsubstituted or N-substituted carbamoyl group, an ester group or a carboxyl group. Of these, an N-unsubstituted or N-substituted carbamoyl group is preferred.
An N-unsubstituted carbamoyl group is a group represented by —CONH$_2$. An N-substituted carbamoyl group may have either one or two N-substituents. In other words, an N-substituted carbamoyl group is a group represented by either —CONHR$^{31}$ or —CONR$^{31}$R$^{311}$. The N-substituents $R^{31}$ and $R^{311}$ in a group represented by —CONR$^{31}$R$^{311}$ may be the same or different. There are no particular limitations on the N-substituents $R^{31}$ and $R^{311}$, and examples include alkyl groups such as a methyl group, an ethyl group, an n-propyl group, an isopropyl group, an n-butyl group, an isobutyl group, a t-butyl group, a pentyl group or a hexyl group; halogenoalkyl groups such as a chloromethyl group, a fluoromethyl group, a difluoromethyl group or a chloroethyl group; aralkyl groups such as a benzyl group, a 4-methoxybenzyl group, a 2,4-dimethoxybenzyl group, a diphenylmethyl group, a trityl group or a phenethyl group; alkoxyalkyl groups such as a methoxymethyl group; aralkyloxyalkyl groups such as a benzyloxymethyl group; substituted siloxyalkyl groups such as a t-butyldimethylsiloxymethyl group; alkoxy groups such as a methoxy group, an ethoxy group, a propoxy group, an isopropoxy group, a butoxy group, an isobutoxy group, a t-butoxy group, a pentyloxy group or a hexyloxy group; aralkyloxy groups such as a benzyloxy group, a diphenylmethyloxy group or a trityloxy group; substituted silyl groups such as a t-butyldimethylsilyl group; aryl groups such as a phenyl group, a naphthyl group, an indanyl group, an indenyl group, a 4-methoxyphenyl group, a 4-methoxymethylphenyl group, a 2-methoxy-1-naphthyl group or a 2-pyridyl group; and acyl groups such as a formyl group, an acetyl group, a butyryl group, an ethylcarbonyl group, a trichloroethoxycarbonyl group, a trifluoroacetyl group, a t-butoxycarbonyl group or a benzyloxycarbonyl group. Further, $R^{31}$ and $R^{311}$ may be bonded together to form a ring with the adjacent N-atom.
An ester group is a group represented by —COOR$^{32}$. There are no particular limitations on the substituent $R^{32}$, and examples include alkyl groups such as a methyl group, an ethyl group, an n-propyl group, an isopropyl group, an n-butyl group, an isobutyl group, a t-butyl group, a pentyl group or a hexyl group; and halogenoalkyl groups such as a chloromethyl group, a fluoromethyl group, a difluoromethyl group or a chloroethyl group. A carboxyl group is a group in which $R^{32}$ is a hydrogen atom.
There are no particular limitations on the method used for producing the hydroxypyrazine derivative represented by formula (I), but the method for producing a hydroxypyrazine derivative according to the present invention described below is preferred.

Examples of the chlorinating agent include simple chlorine (molecular chlorine), N-chlorosuccinimide, phosphorus pentachloride, phosphoryl chloride, phosphorus oxychloride, thionyl chloride, phosgene, diphosgene, triphosgene, hypochlorite salts, cyanuric chloride, 1,3-dialkyl-2-chloroimidazolinium chloride and 2-chloro-1,3-dimethylbenzimidazolium chloride. Of these, anhydrous chlorinating agents such as phosphorus oxychloride, thionyl chloride, phosgene, diphosgene and triphosgene are particularly preferred.

The amount used of the chlorinating agent is usually within a range from 2 to 10 mols, and preferably from 2 to 5 mols, per 1 mol of the hydroxypyrazine derivative represented by formula (I).

The reaction between the hydroxypyrazine derivative represented by formula (I) and the chlorinating agent is usually conducted either without a solvent, or within a solvent.

There are no particular limitations on the solvent, provided it is an inert solvent that has no adverse effect on the chlorination reaction. Examples of the solvent include ester-based solvents such as ethyl acetate, isopropyl acetate and n-butyl acetate; ketone-based solvents such as acetone, methyl ethyl ketone, methyl isobutyl ketone and cyclohexanone; saturated hydrocarbon-based solvents such as n-pentane, n-hexane, cyclohexane, methylcyclohexane and n-heptane; nitrile-based solvents such as acetonitrile and benzonitrile; ether-based solvents such as diethyl ether, diisopropyl ether, dioxane, tetrahydrofuran and 1,2-dimethoxyethane; sulfur-containing solvents such as dimethyl sulfoxide and sulfolane; amide-based solvents such as N,N-dimethylformamide, N,N-dimethylacetamide and hexamethylphosphoramide; halogenated hydrocarbon-based solvents such as methylene chloride, chloroform, carbon tetrachloride and 1,2-dichloroethane; and aromatic hydrocarbon-based solvents such as benzene, toluene and monochlorobenzene. These solvents may be used individually or in combinations containing two or more different solvents. Of these solvents, nitrile-based solvents and aromatic hydrocarbon-based solvents and the like are preferred.

In those cases where a solvent is used, the amount of the solvent is usually within a range from 0.001 to 100 parts by mass per 1 part by mass of the hydroxypyrazine derivative represented by formula (I).

The above-mentioned reaction is preferably conducted in the presence of a base.

Examples of the base include alkyl amines such as trimethylamine, diethylamine, triethylamine, diisopropylamine and diisopropylethylamine; aryl amines such as aniline and N,N-dimethylaniline; heterocyclic amines such as pyridine, 1,8-diazabicyclo[5.4.0]undec-7-ene (DBU) and 1,5-diazabicyclo[4.3.0]non-5-ene (DBN); and inorganic bases such as sodium carbonate and potassium carbonate. Of these, a tertiary alkyl amine or heterocyclic amine is preferred, and triethylamine, diisopropylethylamine and pyridine and the like are particularly preferred.

The amount used of the base is usually within a range from 2 to 10 mols, and preferably from 2 to 5 mols, per 1 mol of the hydroxypyrazine derivative represented by formula (I).

The reaction temperature is usually within a range from 0° C. to 200° C., and preferably from 50° C. to 150° C. The reaction time varies depending on the reaction scale, but is usually within a range from 5 minutes to several days.

Following completion of the reaction, typical post-processing operations or product purification may be performed. There are no particular limitations on the purification method used, and conventional methods such as distillation, recrystallization or column chromatography may be used.

By using the method described above, a dichloropyrazine derivative represented by formula (II) can be obtained. In the formula (II), $R^{21}$ represents a nitrile group, an N-unsubstituted or N-substituted carbamoyl group, an ester group, a carboxyl group, or a group formed as a result of a change in the functional group of $R^2$ during chlorination. For example, when the functional group $R^2$ is a carbamoyl group, the chlorination step described above may result in the carbamoyl group changing to a nitrile group as $R^{21}$.

<Method for Producing Hydroxypyrazine Derivative>

The starting raw material for the production method of the present invention, namely the hydroxypyrazine derivative represented by formula (I), is preferably produced using the method described below.

Namely, the method for producing a hydroxypyrazine derivative according to the present invention includes reacting a pyrazine derivative represented by formula (III) with a halogenating agent.

In formula (III), $R^2$ represents a nitrile group, an N-unsubstituted or N-substituted carbamoyl group, an ester group or a carboxyl group. $R^2$ in formula (III) may be selected from those substituents corresponding with $R^2$ in formula (I), which represents the targeted hydroxypyrazine derivative.

M is a cation capable of forming a salt. n represents a number corresponding with the valence of M, and can usually be represented by an integer. For example, when the valence of M is 1, n represents 1, whereas when the valence of M is 2, n represents 2.

Examples of M include cations formed from a metal element belonging to group I, a metal element belonging to group IIa or a metal element belonging to group IIIa of the periodic table of elements; a cation formed from a transition metal element such as iron or copper; an ammonium salt cation; and a cation foamed from an organic base such as trimethylamine, triethylamine, tributylamine, pyridine, N,N-dimethylaniline, N-methylpiperidine, N-methylmorpholine, dicyclohexylamine, procaine, dibenzylamine, N-benzyl-β-phenethylamine, 1-ephenamine, N,N'-dibenzylethylenediamine or hydrazine. In this description, the expression "cation formed from ~" means a cation formed by ionization of an above-mentioned metal element or organic base.

Of these cations, a cation formed from a metal element belonging to group I, group IIa or group IIIa of the periodic table of elements is preferred.

The metal elements belonging to group I are known as the alkali metals (lithium, sodium, potassium, rubidium and cesium). Of these, sodium or potassium or the like is preferred.

The metal elements belonging to group IIa are beryllium, magnesium, calcium, strontium, barium and radium. Of these, magnesium or calcium or the like is preferred.

The metal elements belonging to group IIIa are boron, aluminum, gallium, indium and thallium. Of these, boron or aluminum is particularly preferred.

Among the above options, M is preferably a cation formed from an alkali metal element, and is most preferably a cation formed from sodium or potassium or the like.

Examples of the halogenating agent include simple chlorine (molecular chlorine), simple bromine (molecular bromine), simple iodine (molecular iodine), N-chlorosuccinimide, N-bromosuccinimide, phosphorus pentachloride, phosphoryl chloride, phosphorus oxychloride, thionyl chloride, hypochlorite salts, hypobromite salts, cyanuric chloride, bis(2,4,6-trimethylpyridine)bromonium hexafluorophosphate, bis(2,4,6-trimethylpyridine)iodonium hexafluorophosphate, 1,3-dialkyl-2-halogenoimidazolinium halides and 2-chloro-1,3-dimethylbenzimidazolium chloride. Of these, simple chlorine or simple bromine is preferred, and simple bromine is particularly preferred.

The amount used of the halogenating agent is usually within a range from 1 to 5 mols, and preferably from 1.1 to 2 mols, per 1 mol of the pyrazine derivative represented by formula (III).

The reaction between the pyrazine derivative represented by formula (III) and the halogenating agent is usually conducted in a solvent. There are no particular limitations on the solvent, provided it is an inert solvent that has no adverse effect on the halogenation reaction. Examples of the solvent include water; acetic acid; alcohol-based solvents such as methanol, ethanol and isopropyl alcohol; ester-based solvents such as ethyl acetate, isopropyl acetate and n-butyl acetate; ketone-based solvents such as acetone, methyl ethyl ketone, methyl isobutyl ketone and cyclohexanone; saturated hydrocarbon-based solvents such as n-pentane, n-hexane, cyclohexane, methylcyclohexane and n-heptane; nitrile-based solvents such as acetonitrile and benzonitrile; ether-based solvents such as diethyl ether, diisopropyl ether, dioxane, tetrahydrofuran and 1,2-dimethoxyethane; sulfur-containing solvents such as dimethyl sulfoxide and sulfolane; amide-based solvents such as N,N-dimethylformamide, N,N-dimethylacetamide and hexamethylphosphoramide; and halogenated hydrocarbon-based solvents such as methylene chloride, chloroform, carbon tetrachloride and 1,2-dichloroethane. These solvents may be used individually or in combinations containing two or more different solvents.

Of these solvents, alcohol-based solvents, ester-based solvents and nitrile-based solvents and the like are preferred, and from the viewpoint of achieving favorable solubility of the pyrazine derivative represented by formula (III), a mixed solvent of two or more solvents including an alcohol-based solvent is particularly preferred.

The amount used of the solvent is usually within a range from 0.001 to 100 parts by mass per 1 part by mass of the pyrazine derivative represented by formula (III).

The reaction temperature is usually within a range from −20° C. to 100° C., and preferably from 0° C. to 50° C. The reaction time varies depending on the reaction scale, but is usually within a range from 5 minutes to several days.

Following completion of the reaction, typical post-processing operations or product purification may be performed. There are no particular limitations on the purification method used, and conventional methods such as distillation, recrystallization or column chromatography may be used.

As described above, by employing the present invention, a hydroxypyrazine derivative represented by formula (I) can be produced efficiently by reacting a pyrazine derivative represented by formula (III), namely a pyrazine derivative (III) that exists as a salt containing a cation M, with a halogenating agent. Moreover, by reacting the hydroxypyrazine derivative represented by formula (I) with a chlorinating agent, a dichloropyrazine derivative represented by formula (II) that is useful as a production intermediate for antiviral agents and the like can be obtained.

By fluorinating a dichloropyrazine derivative represented by formula (II) obtained using the production method of the present invention, a fluorinated compound typified by the compound represented by formula (IX) can be obtained. Moreover, by subsequently hydroxylating the fluorinated compound, and then, for example in those cases where the group corresponding with $R^{21}$ is a nitrile group, amidating the nitrile group, a compound typified by the compound represented by formula (XI) can be obtained.

The pyrazine derivative represented by formula (III) can be readily obtained using conventional methods, using the method disclosed in the examples below or related methods, or by using an appropriate combination of these methods.

EXAMPLES

The present invention is described below in further detail using a series of examples. However, the present invention is in no way limited by these examples.

The equipment used in the high-performance liquid chromatography (HPLC) analyses and $^1$H-NMR measurements described in the examples was as follows: [HPLC Analyses] Pump: LC-10ATvp, detector: SPD-10Avp, thermostatic oven: CTO-10ACvp, chromatopack: CR-8A, all manufactured by Shimadzu Corporation. [$^1$H-NMR measurements] FT-NMR, JNM-AL400, manufactured by MOL Ltd.

Example 1

Synthesis (1) of 6-bromo-3-hydroxypyrazine-2-carboxamide

Step 1: Synthesis of sodium 2-carbamoylpyrazine-3-hydroxylate 231.5 g of an 18% aqueous solution of sodium hydroxide was cooled to −10° C., and 97.3 g of 2-aminomalonic acid diamide was then suspended in the solution. Subsequently, 148.4 g of a 40% aqueous solution of glyoxal was added dropwise to the suspension over a period of 40 minutes. Following completion of the dropwise addition, the reaction mixture was stirred for one hour at −5° C., and was then heated to 22° C. and stirred for a further 3 hours. The reaction mixture was then cooled to a temperature of not more than 5° C., and the solid product was filtered off, washed with 166 ml of an 80% aqueous solution of acetonitrile, and then washed with 166 ml of acetonitrile, yielding 149.0 g (yield: 92.0%) of sodium 2-carbamoylpyrazine-3-hydroxylate.

Step 2: Synthesis of 6-bromo-3-hydroxypyrazine-2-carboxamide 149.0 g of the sodium 2-carbamoylpyrazine-3-hydroxylate obtained in the above-described step 1 was suspended in a mixed solvent containing 153 ml of methanol and 612 ml of acetonitrile. Subsequently, 152.8 g of bromine was added dropwise to the suspension at 15 to 24° C. over a period of 8 minutes, and the resulting mixture was stirred for one hour at 20 to 24° C. The reaction mixture was then cooled to 0° C., 1,529 ml of water was added dropwise, and following completion of the dropwise addition, the mixture was stirred for a further one hour at 0° C. The solid product was filtered off and washed with 765 ml of water, yielding 126.0 g (yield: 75.6%) of 6-bromo-3-hydroxypyrazine-2-carboxamide.

Example 2

Synthesis (2) of 6-bromo-3-hydroxypyrazine-2-carboxamide 1.62 g of sodium 2-carbamoylpyrazine-3-hydroxylate was suspended in a mixed solvent containing 20 ml of methanol and 80 ml of ethyl acetate. Subsequently, 2.16 g of bromine was added dropwise to the suspension at 16 to 17° C. over a period of 10 minutes, and the resulting mixture was stirred for one hour at 18 to 19° C. 20 ml of water was then added, and the reaction mixture was stirred for a further 15 minutes. Subsequently, the reaction mixture was concentrated under reduced pressure at 40° C. until the weight of residual liquid was reduced to 16.8 g. The mixture was then cooled to 5° C., and the solid product was filtered off and washed with 40 ml of water, yielding 1.64 g (yield: 75.2%) of 6-bromo-3-hydroxypyrazine-2-carboxamide.

Comparative Example 1

Synthesis (3) of 6-bromo-3-hydroxypyrazine-2-carboxamide 139 mg of 3-hydroxypyrazine-2-carboxamide was suspended in 10 ml of acetonitrile. The suspension was cooled to 0° C., 0.28 g of bromine was added, and the resulting mixture was stirred for 2 hours at 0° C., a further 2.5 hours at room temperature, and then a further 1.5 hours at 40° C. Analysis of the reaction mixture by HPLC revealed a total peak area ratio between 6-bromo-3-hydroxypyrazine-2-carboxamide and 3-hydroxypyrazine-2-carboxamide of 1:10.5.

Example 3

Synthesis of 3,6-dichloropyrazine-2-carbonitrile 2.18 g of 6-bromo-3-hydroxypyrazine-2-carboxamide was suspended in 10 ml of monochlorobenzene, and 6.13 g of phosphorus oxychloride was then added to the suspension. The resulting mixture was heated to 60° C., and stirred for 30 minutes at 60° C. Subsequently, 3.88 g of diisopropylethylamine was added dropwise to the mixture over a period of 10 minutes. The mixture was then stirred for a further 2.5 hours at a temperature of 90 to 100° C. Following cooling to room temperature, 20 ml of toluene was added to the reaction mixture, and a distillation was then performed under reduced pressure. The distillation was continued until no more distillate was produced, 20 ml of toluene and 10 ml of water were then added to the residue, the resulting mixture was stirred at 40° C. for 2.5 hours, and a separation was then performed. The organic layer was washed with water, washed with a 5% solution of sodium bicarbonate, and then washed with a 10% saline solution, yielding a toluene solution of 3,6-dichloropyrazine-2-carbonitrile. Quantitative analysis using HPLC revealed an equivalent yield of pure 3,6-dichloropyrazine-2-carbonitrile of 1.44 g (yield: 83.0%).

Reference Example

Synthesis of 6-fluoro-3-hydroxypyrazine-2-carboxamide

Step 1: Synthesis of 3,6-difluoropyrazine-2-carbonitrile 3.49 g of potassium fluoride and 1.33 g of tetrabutylammonium bromide were suspended in a mixed solvent containing 40 ml of toluene and 20 ml of dimethyl sulfoxide. The toluene was subsequently removed by distillation at normal pressure. A further 40 ml of toluene was then added and once again removed by distillation, thereby removing moisture from the system. 14.08 g of a toluene solution of 3,6-dichloropyrazine-2-carbonitrile with a concentration of 24.7% was then added to the reaction system, and the resulting mixture was stirred at 60° C. for 2.5 hours. Subsequently, 20 ml of toluene and 30 ml of water were added, and a separation was performed. The organic layer was washed with 20 ml of water, 20 ml of water and concentrated hydrochloric acid were then added to the organic layer to adjust the pH to 1.6, and another separation was performed. The organic layer was then washed with 20 ml of a 5% saline solution. Quantitative analysis by HPLC of the obtained organic layer revealed an equivalent yield of pure 3,6-difluoropyrazine-2-carbonitrile of 2.60 g (yield: 92.3%).

Step 2: Synthesis of 6-fluoro-3-hydroxypyrazine-2-carbonitrile

To 19.92 g of a toluene solution of 3,6-difluoropyrazine-2-carbonitrile with a concentration of 12.7% were sequentially added 18 ml of dimethyl sulfoxide, 9 ml of water, and 2.95 g of sodium acetate. The resulting mixture was heated to 50° C., and stirred at 50° C. for 7 hours. The mixture was then cooled to room temperature, and 9 ml of water and concentrated hydrochloric acid were added to adjust the pH to 2.5. 54 ml of ethyl acetate was added and a separation was performed. The separated organic layer was washed with 18 ml of water, and then washed with a 10% saline solution. Each of the aqueous layers was extracted with 18 ml of ethyl acetate, and the thus obtained organic layers were combined with the original organic layer. The ethyl acetate was then removed by distillation under reduced pressure, yielding 3.45 g of an oily 6-fluoro-3-hydroxypyrazine-2-carbonitrile.

Step 3: Synthesis of 6-fluoro-3-hydroxypyrazine-2-carboxamide 14.39 g of concentrated sulfuric acid was added to 3.45 g of the oily 6-fluoro-3-hydroxypyrazine-2-carbonitrile, and the resulting mixture was stirred at 50° C. for 4 hours. The reaction mixture was then added dropwise over a period of 20 minutes to 44.5 ml of water that had been cooled to 3° C. Following completion of the dropwise addition, the resulting mixture was stirred for 20 minutes at a temperature of not more than 10° C. Subsequently, 10.17 g of a 28% aqueous solution of sodium hydroxide was added dropwise to the reaction mixture over a period of 15 minutes. Following completion of the dropwise addition, the mixture was stirred at the same temperature for 30 minutes. The solid product was then filtered off, and washed with 18 ml of water, yielding 2.22 g (yield: 92.3%) of 6-fluoro-3-hydroxypyrazine-2-carboxamide.

INDUSTRIAL APPLICABILITY

The production method of the present invention does not include a nitration reaction that suffers from a danger of explosion, and therefore can be performed without requiring explosion-proof equipment or the like, even in the case of industrial production. According to the production method of the present invention, a dichloropyrazine derivative that is useful as an intermediate for agrochemicals or pharmaceutical products such as antiviral agents, and a hydroxypyrazine derivative that functions as an intermediate for the dichloropyrazine derivative can be obtained at low cost, with comparative ease, and in high yield.

The invention claimed is:

1. A method for producing a dichloropyrazine derivative represented by formula (II):

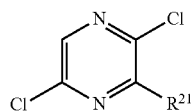

wherein $R^{21}$ represents a nitrile group, an N-unsubstituted or N-substituted carbamoyl group, an ester group, a carboxyl group, or an acid chloride, the method comprising reacting a hydroxypyrazine derivative represented by formula (I):

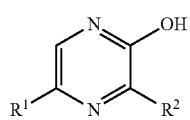

wherein $R^1$ represents a halogen atom, and $R^2$ represents a nitrile group, an N-unsubstituted or N-substituted carbamoyl group, an ester group or a carboxyl group, with a chlorinating agent.

2. A method for producing a dichloropyrazine-derivative, represented by formula (II)

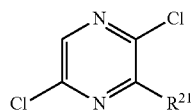

wherein $R^{21}$ represents a nitrile group, an N-unsubstituted or N-substituted carbamoyl group, an ester group, a carboxyl group, or an acid chloride, the method comprising reacting a pyrazine derivative represented by formula (III):

wherein $R^2$ represents a nitrile group, an N-unsubstituted or N-substituted carbamoyl group, an ester group or a carboxyl group, M represents a cation capable of forming a salt, and n represents a number corresponding with a valence of M, with a halogenating agent, to obtain a hydroxypyrazine derivative represented by formula (I):

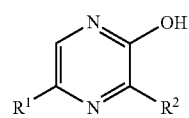

wherein $R^1$ represents a halogen atom, and $R^2$ represents a nitrile group, an N-unsubstituted or N-substituted carbamoyl group, an ester group or a carboxyl group, and then reacting a hydroxypyrazine derivative represented by formula (I) with a chlorinating agent.

* * * * *